US 9,050,425 B2

(12) United States Patent
Van Der Mark

(10) Patent No.: US 9,050,425 B2
(45) Date of Patent: Jun. 9, 2015

(54) MAGNETIC COUPLING FOR AEROSOL GENERATING APPARATUS

(75) Inventor: Martinus Bernardus Van Der Mark, Best (NL)

(73) Assignee: Koninklijke Philips N.V., Eindhoven (NL)

( * ) Notice: Subject to any disclaimer, the term of this patent is extended or adjusted under 35 U.S.C. 154(b) by 464 days.

(21) Appl. No.: 13/521,292

(22) PCT Filed: Dec. 8, 2010

(86) PCT No.: PCT/IB2010/055676
§ 371 (c)(1),
(2), (4) Date: Jul. 10, 2012

(87) PCT Pub. No.: WO2011/083380
PCT Pub. Date: Jul. 14, 2011

(65) Prior Publication Data
US 2012/0285446 A1    Nov. 15, 2012

Related U.S. Application Data

(60) Provisional application No. 61/293,746, filed on Jan. 11, 2010.

(51) Int. Cl.
*A61M 11/00* (2006.01)
*A61M 15/00* (2006.01)
(Continued)

(52) U.S. Cl.
CPC .............. *A61M 15/001* (2014.02); *A61M 11/00* (2013.01); *A61M 15/00* (2013.01);
(Continued)

(58) Field of Classification Search
CPC .............. A61M 15/00; A61M 11/005; A61M 11/006; A61M 11/02; A61M 15/0001; A61M 15/0005; A61M 15/001; A61M 15/0021; A61M 15/0085; A61M 15/0086; A61M 15/02; A61M 15/025; A61M 15/06; A61M 15/08; B05B 17/06; B05B 17/0607; B65D 83/752; B65D 83/75
USPC ............. 128/200.14, 200.15, 200.16, 200.17, 128/200.18, 200.19, 200.2, 200.21, 200.22, 128/200.23, 203.12, 203.14, 203.15, 128/203.19, 203.24, 204.14; 222/635, 222/402.1, 402.11, 402.24, 402.14, 510, 222/507, 402.18, 198, 201, 202, 203; 239/102.1, 338, 102.2
See application file for complete search history.

(56) References Cited

U.S. PATENT DOCUMENTS

| 4,057,807 | A | | 11/1977 | Fischbeck et al. |
| 4,152,476 | A | * | 5/1979 | Stillman ........................ 428/189 |
| 5,823,434 | A | * | 10/1998 | Cooper ....................... 239/102.2 |
| 5,838,350 | A | | 11/1998 | Newcombe et al. |
| 6,328,033 | B1 | * | 12/2001 | Avrahami ................. 128/203.15 |
| 6,722,582 | B2 | | 4/2004 | Hess et al. |
| 6,748,944 | B1 | | 6/2004 | Della Vecchia et al. |
| 6,901,926 | B2 | | 6/2005 | Yamamoto et al. |
| 7,891,580 | B2 | * | 2/2011 | Valpey et al. ............... 239/102.2 |

(Continued)

FOREIGN PATENT DOCUMENTS

| EP | 0739654 A2 | 10/1996 |
| EP | 2022526 A1 | 2/2009 |
| WO | 2009150619 A1 | 12/2009 |

OTHER PUBLICATIONS

Schipper, "Respironics I-NEB II Design Descriptions" APT513-08-5484 C07 Philips Applied Technologies, Jan. 17, 2009.

*Primary Examiner* — Valerie L Skorupa
*Assistant Examiner* — Tu Vo

(57) ABSTRACT

An apparatus (e.g., nebulizer) for aerosol delivery of a substance (e.g., a drug to a patient) has a mouthpiece (36); a chamber (34) holding a substance; a flexible membrane (38) having a plurality of apertures; and a vibrator (20) for vibrating the flexible membrane to form a flow of aerosol droplets of the substance that are ejected through the apertures and to the mouthpiece. The vibrator may be a piezoelectric element. A magnetic member (54) is provided on the flexible membrane and is configured to magnetically couple the flexible membrane to the vibrator. The magnetic member allows replacement of the membrane, without wasting the piezoelectric element.

31 Claims, 6 Drawing Sheets

(51) Int. Cl.
  *B05B 17/06* (2006.01)
  *B05B 17/00* (2006.01)
  *B65D 83/14* (2006.01)
  *A61M 16/00* (2006.01)

(52) U.S. Cl.
  CPC ...... *A61M 15/0001* (2014.02); *A61M 15/0021* (2014.02); *A61M 15/0005* (2014.02); *B65D 83/752* (2013.01); *B65D 83/75* (2013.01); *B05B 17/06* (2013.01); *B05B 17/0607* (2013.01); *A61M 11/005* (2013.01); *A61M 15/0085* (2013.01); *A61M 2016/0021* (2013.01); *A61M 2205/0272* (2013.01); *A61M 2205/12* (2013.01); *A61M 2205/14* (2013.01); *A61M 2205/502* (2013.01); *A61M 2205/52* (2013.01); *A61M 2205/581* (2013.01); *A61M 2205/8206* (2013.01); *B05B 17/0646* (2013.01)

(56) References Cited

U.S. PATENT DOCUMENTS

| | | |
|---|---|---|
| 2003/0080214 A1 | 5/2003 | Hess et al. |
| 2003/0196660 A1* | 10/2003 | Haveri ..................... 128/203.12 |
| 2004/0107963 A1* | 6/2004 | Finlay et al. ............. 128/203.15 |
| 2004/0139963 A1 | 7/2004 | Ivri et al. |
| 2005/0230495 A1 | 10/2005 | Feriani et al. |
| 2007/0189919 A1 | 8/2007 | Prince et al. |
| 2008/0308096 A1* | 12/2008 | Borgschulte et al. .... 128/200.14 |
| 2009/0242660 A1 | 10/2009 | Yu |
| 2010/0024812 A1* | 2/2010 | Sugita et al. ............. 128/203.12 |
| 2010/0083956 A1* | 4/2010 | Fukumoto et al. ....... 128/200.14 |

* cited by examiner

MAGNETIC COUPLING FOR AEROSOL GENERATING APPARATUS

The present invention is generally related to an apparatus for delivering an aerosolized liquid or substance Devices for generating and delivering an aerosolized liquid or substance are used for various applications. For example, they can be used to deliver aerosolized medicine, or can be used to generate steam in other devices such as irons.

Medical devices used to deliver drugs in an aerosol form to patients have been used since the mid 1950s. Such devices are used to deliver inhaled pharmaceutical aerosols (IPAs) into lungs of patients to treat asthma, cystic fibrosis, and chronic obstructive pulmonary diseases (COPD), for example. Nebulizers are one type of device used for the delivery of aerosolized medicine. Nebulizers may use different types of mechanisms for aerosolizing medicine. An ultrasonic nebulizer employs an electrical source to provide energy to a vibratable element which generates high frequency vibrations. These vibrations cause small droplets of a medicine or liquid to form into an aerosol. Some nebulizers may employ a mesh having a number of apertures therein. When a vibration is induced in the mesh, a liquid with medicine may be delivered through the apertures in aerosol form to the mouthpiece and thus the patient. Generally, disposal of the mesh membrane is undesirable, as the vibratable element is made with a high quantity of lead, which can pollute the environment.

The company Quatek (of Taiwan) has a nebulizer, for example, MODEL NE403, which has a central functional part consisting of a 15 mm (hard) piezoelectric ring with a disk-shaped stainless steel spring glued on top. In the center of the device is a mesh membrane, with holes for producing a mist or aerosol, that is glued to the stainless steel spring. However, a mesh membrane, such as the one provided in the above Quatek device, is susceptible to deterioration over time, due to pollution by bacteria, inorganic contaminants, and/or accumulation of medicine on the mesh, for example. Such deterioration in the mesh decreases the effectiveness of the nebulizer. Cleaning of the mesh membrane is difficult and cumbersome, if possible at all.

One aspect of the invention, there is provided an apparatus for aerosol delivery of a substance having: a mouthpiece; a chamber for holding a liquid substance therein; a flexible membrane with a plurality of apertures therethrough; and a vibrator for vibrating the flexible membrane. The flexible membrane is made from a magnetic material that enables the flexible membrane to be coupled to the vibrator such that when the flexible membrane is vibrated by the vibrator a flow of aerosol droplets of the substance are ejected through the plurality of apertures and to the mouthpiece for delivery therefrom.

Another aspect of the invention includes a removable insert configured to be removably inserted into an apparatus for aerosol delivery of a substance. The apparatus has a vibrator. The removable insert has: a body; a flexible membrane with a plurality of apertures therethrough, and an attachment member for attaching the flexible membrane to the body. The flexible membrane is configured to be vibrated by the vibrator when the removable insert is inserted into the apparatus such that a flow of aerosol droplets of the substance are ejected through the plurality of apertures for delivery out of the apparatus.

Yet another aspect of the invention includes an apparatus for aerosol generation, the apparatus having: a chamber for holding a liquid substance therein; a flexible membrane with a plurality of apertures therethrough; a vibrator for vibrating the flexible membrane; and a magnetic member configured to magnetically couple the flexible membrane to the vibrator such that when the flexible membrane is vibrated by the vibrator a flow of aerosol droplets of the liquid substance are ejected through the plurality of apertures.

These and other objects, features, and characteristics of the present invention, as well as the methods of operation and functions of the related elements of structure and the combination of parts and economies of manufacture, will become more apparent upon considering of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 3:
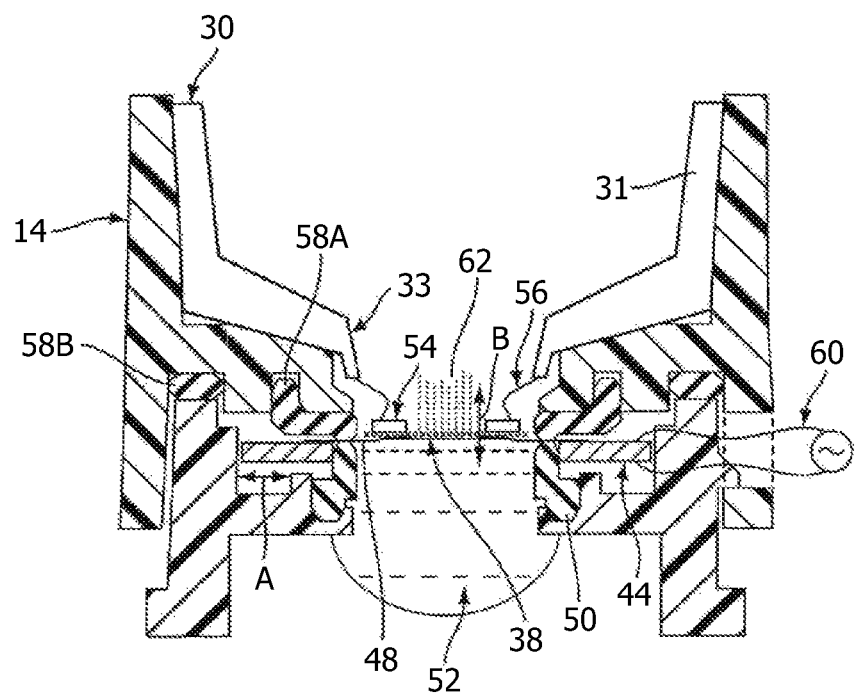
Figure 4:
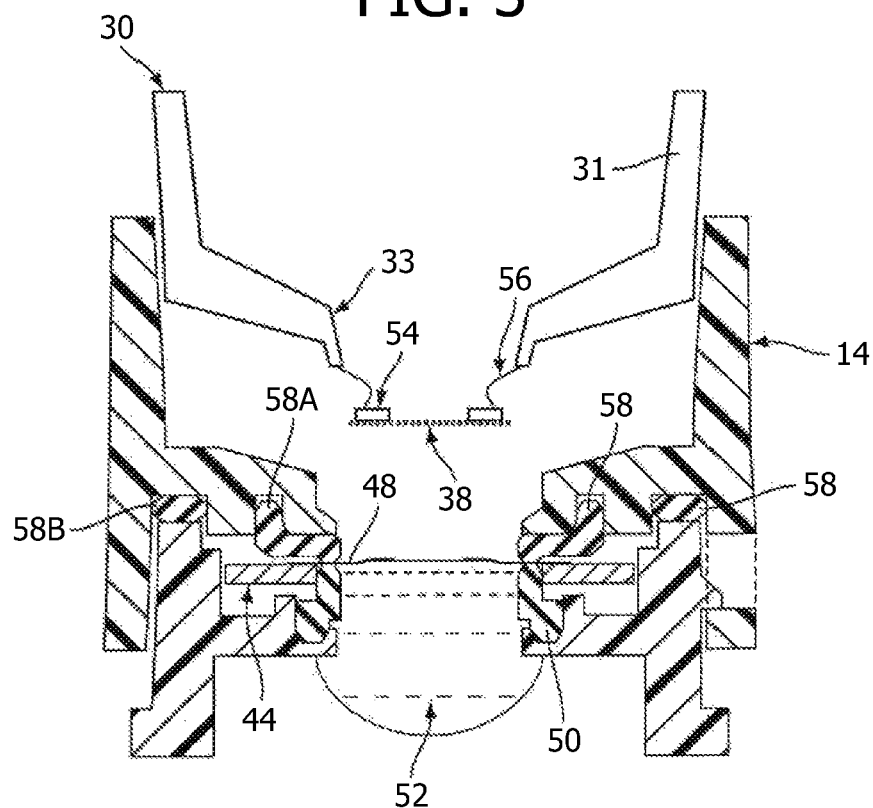

FIGS. 3 and 4 schematically illustrate part of a drug delivery apparatus with a removable insert in accordance with an embodiment.

Figure 5A:
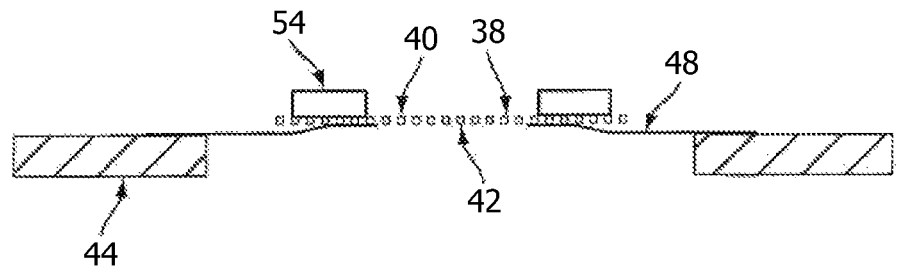

FIG. 5A schematically illustrates part of an embodiment of a drug delivery apparatus including a vibrator, magnetic ring, spring, and flexible membrane.

Figure 5B:
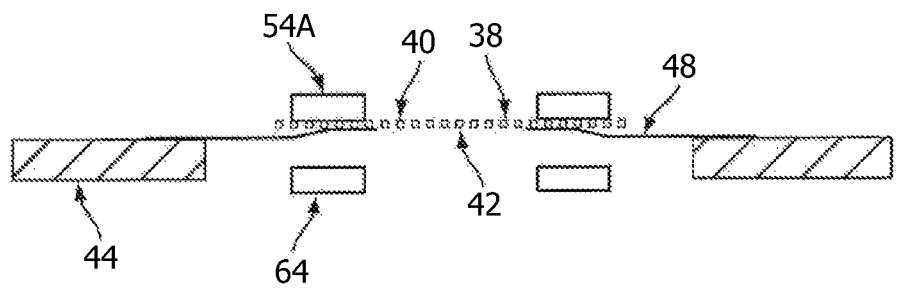

FIG. 5B schematically illustrates part of an embodiment of a drug delivery apparatus including a vibrator, magnetic ring, magnet, spring, and flexible membrane.

Figure 5C:
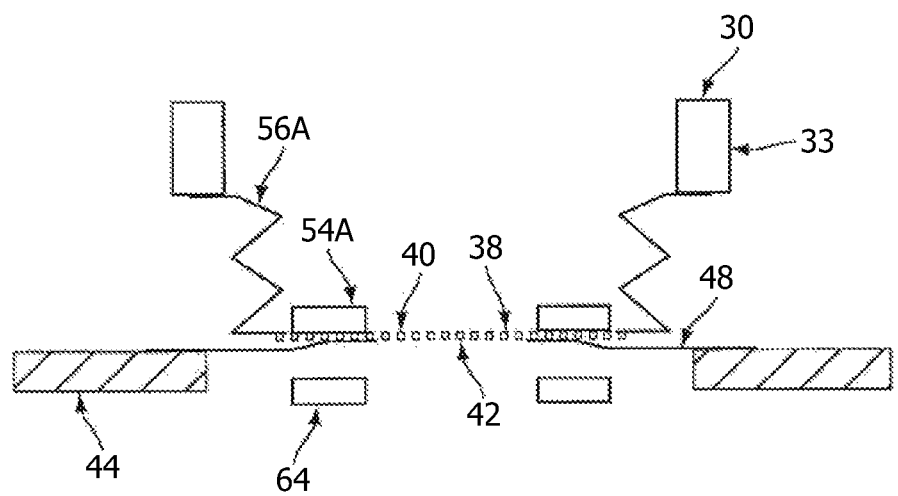

FIG. 5C schematically illustrates part of an embodiment of a drug delivery apparatus including a vibrator, magnetic ring, magnet, spring, and flexible membrane with a removable insert.

Figure 5D:
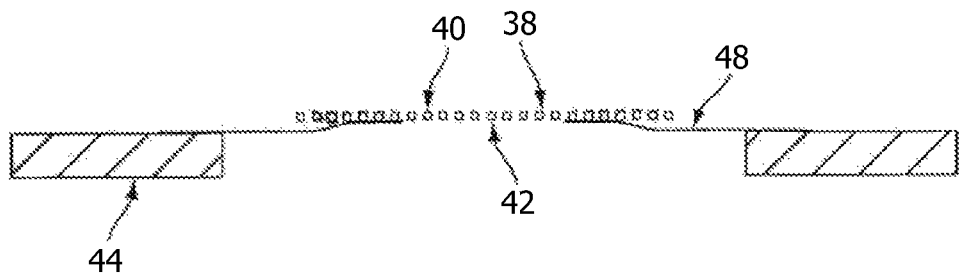

FIG. 5D schematically illustrates part of an embodiment of a drug delivery apparatus including a vibrator, spring, and flexible membrane.

Figure 5E:
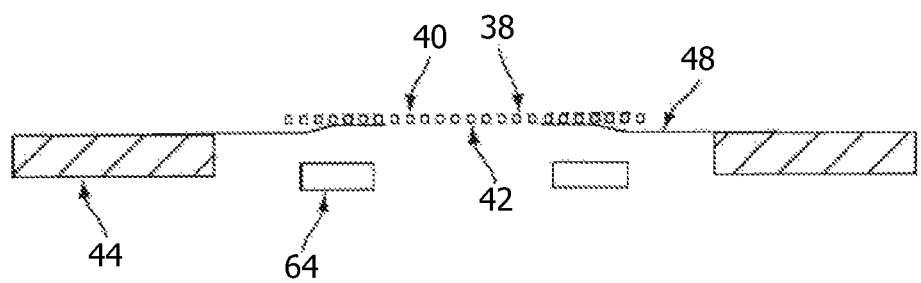

FIG. 5E schematically illustrates part of an embodiment of a drug delivery apparatus including a vibrator, spring, magnet, and flexible membrane.

Figure 6:
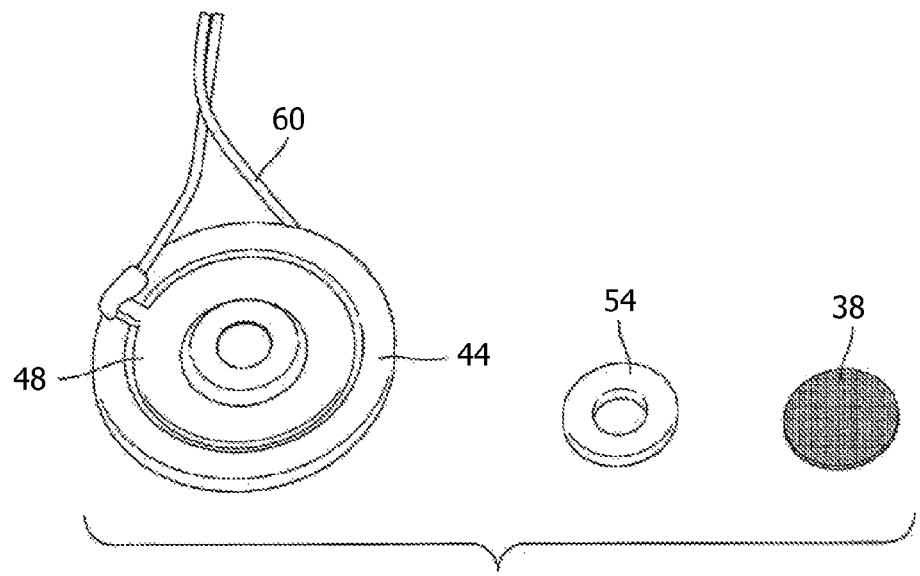

FIG. 6 is a top view of the vibrator, spring, magnetic ring, and flexible membrane in accordance with an embodiment.

Figure 7:
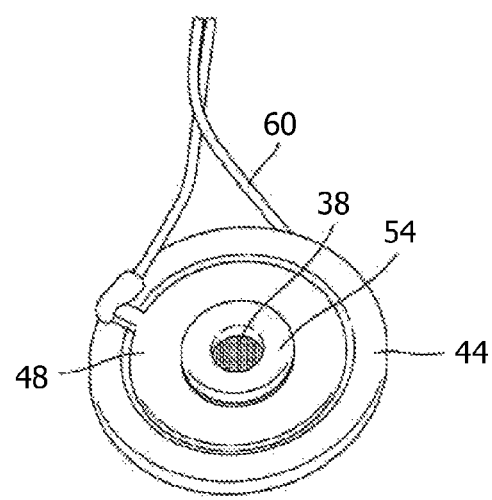

FIG. 7 is a top view of the assembly of the elements of FIG. 6.

Disclosed is an apparatus for delivery of an aerosol substance. In the illustrated embodiment, the apparatus is configured for medical (such as a respiratory drug) delivery to the lungs by aerosol. However, as noted further below, the features (e.g., flexible membrane, magnetic members, etc.) and their use in such an apparatus is not meant to be limiting. Rather, it is envisioned that the herein described features may be used in other apparatuses used for aerosol substance delivery, including, but not limited to, devices for steam delivery (e.g., humidifying devices), devices for moisturizing textiles (e.g., irons), devices for cleaning, and the like. The apparatus is configured to provide small droplets of a liquid (e.g., water) that carry a drug or substance are formed by a combination of a vibrator and a flexible membrane. As noted above, the membrane is subject to deterioration and cleaning is difficult and cumbersome. Thus, separating the vibrator from the membrane is accomplished by coupling the membrane magnetically to the vibrator via a magnetic member.

Figure 1:
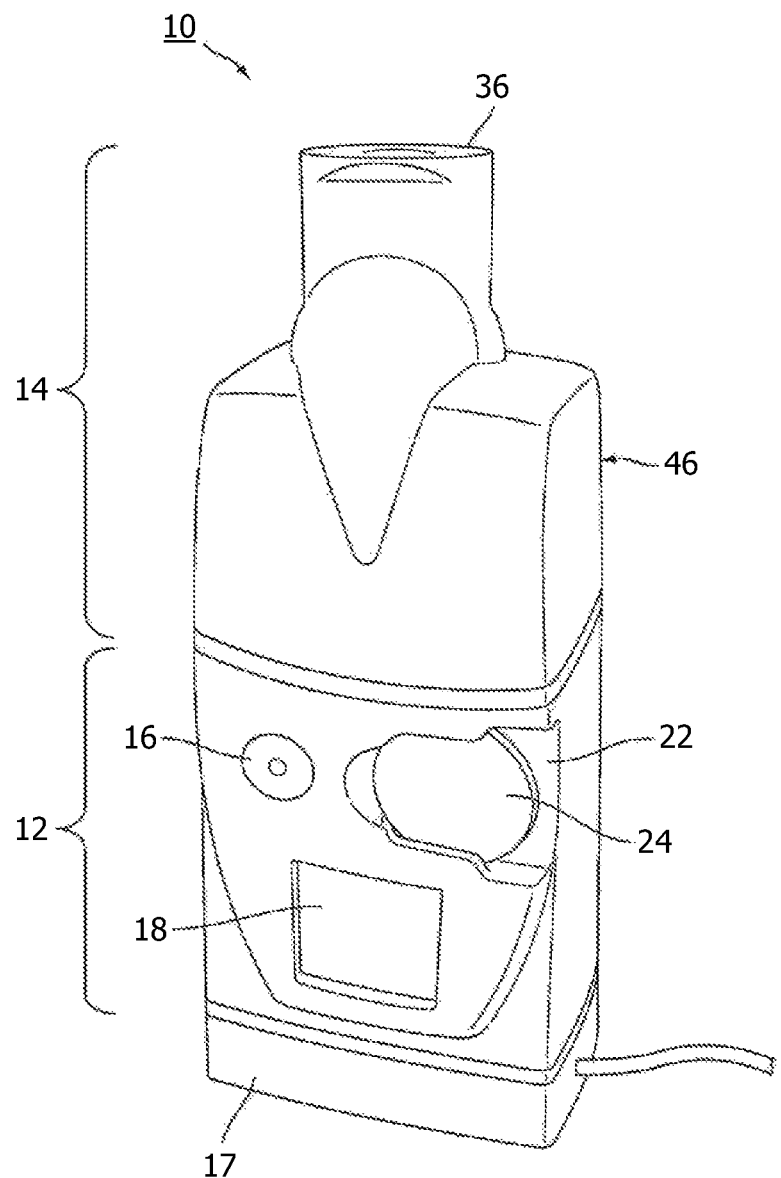
FIG. 1 is a perspective view of a drug delivery apparatus in accordance with an embodiment.
Figure 2:
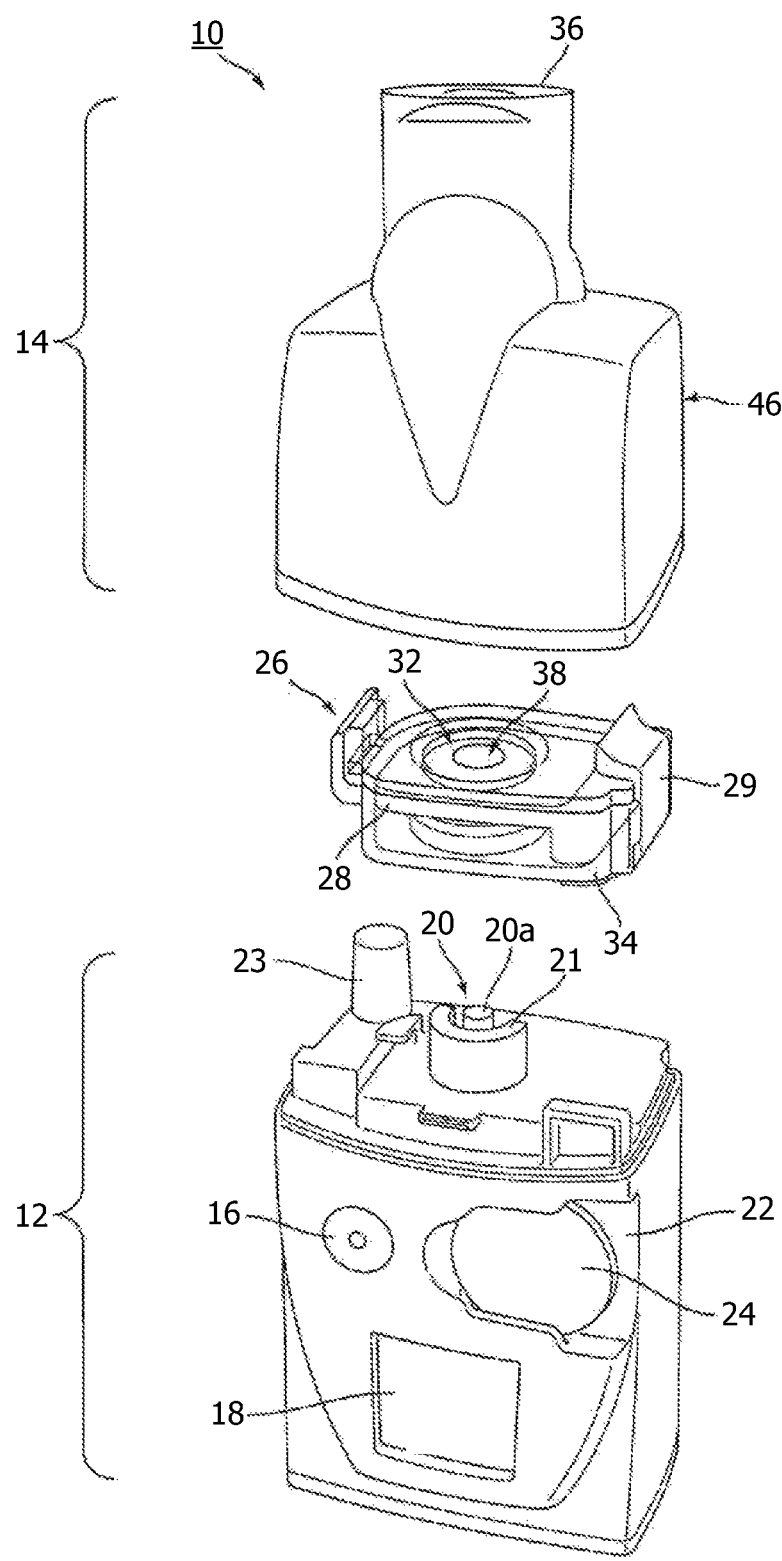
FIG. 2 is an exploded view of the drug delivery apparatus of FIG. 1.

In the illustrated embodiment, as shown in FIG. 1, apparatus 10, also known as a nebulizer, is a compact, lightweight, and portable handheld device. The apparatus 10 is configured to deliver a drug or other therapeutic substance (in the form of a liquid) to a patient in aerosol form during breathing. Apparatus 10 is assembled from a plurality of structural elements. The individual elements may be formed by molding or otherwise formed independently from one another. More specifically, apparatus 10 comprises two parts, a lower portion 12 or body and an upper portion 14. The upper portion 14 and the lower portion 12 are removably connected to each other. In an embodiment, the upper and lower portions may be snap-fit together.

Apparatus 10 and its upper portion 12 and lower portion 14 may be formed from a suitable material. Suitable materials may be any biocompatible material, which is acceptable for a safe and effective use by a patient or a medical professional. Any commonly used material in the art of inhaled pharmaceutical aerosols delivery may be used. Examples of various suitable material may be a plastic, such as a polyethylene, polypropylene, polyurethane, polycarbonate, polysulfone, or a combination thereof.

Parts of the apparatus 10 may be formed by any means in the art used to form nebulizing medical devices. In one embodiment, injection molding may be used to form the lower portion 12 and upper portion 14, for example.

The lower portion 12 includes a power source (not shown) such as a battery pack, an activation button 16 for turning power on/off, a display 18 for displaying information regarding the use of the apparatus 10 (e.g., type and/or amount of drug, error readings, etc.), and a horn device 20 (see FIG. 2). Activation button 16 is a switch for supplying power from the power source to the apparatus 10 and its parts. The power source may be a rechargeable battery that is charged via a universal voltage charger 17, for example. However, other forms of DC power (e.g., 12V) or AC power (e.g., 110V, 120V) may alternatively or optionally be used with apparatus 10. The lower portion 12 may include circuitry (e.g., printed circuit board), a processor and a controller (not shown) in its body, of which power source may supply power to each device. In an embodiment, a memory and/or storage means which may include instructions for delivering an aerosolized drug may also be provided. Instructions may include a dosage amount, dosage frequency, and a number of doses that may be delivered, for example. Alternatively, as noted below, an instruction device, such as disc 24, may include such information. The lower portion 12 of the apparatus 10 may also include a number of parts known in the art for delivering a medicated liquid in aerosol form or assisting a patient during drug administration. Such operating parts are known in the art and therefore are not discussed in detail herein. For example, in an embodiment, the apparatus 10 may include devices for providing an audible feedback in addition to, or as an alternative to, display 18. In another embodiment, one or more sensors (which may include a sensor port cover 23, as shown in FIG. 2) are provided in apparatus 10.

Also provided on lower portion 12 is a disc slot 22 for receiving a disc 24 therein. Disc 24 may comprise data that is placed in disc slot 22 in order to transmit information related to drug treatment as input into the apparatus 10. For example, disc 24 may include information relating to the dosage of the drug, such as an output rate and other variables. Disc 24 may include an antenna and microchip therein that is programmed with information including delivery a pre-set volume of the liquid drug, a dosing frequency, a number of doses, etc. Although disc slot 22 and disc 24 are shown on the outside of the body of lower portion 12, the information related to treatment may also be provided inside the body.

The upper portion 14 includes a detachable mouthpiece 36 for delivering a flow of aerosol at a first end that is in fluid communication with a nebulization chamber 46 at a second end. Inside the upper portion 14 adjacent the mouthpiece 36 is a flap valve (not shown) which is used to assist in detecting a patient's breathing and delivering medication. The nebulization chamber 46 of upper portion 14 houses a medication chamber assembly 26. Medication chamber assembly 26 comprises a chamber lid 28, latch 29, a drug guide 32, and a medication chamber 34, generally shown in the exploded view of FIG. 2. Chamber lid 28 is removable from the body of the medication chamber 34. Chamber lid 28 may be secured to medication chamber 34 via latch 29, for example. In an embodiment, the chamber lid 28 is entirely removable from the body. In another embodiment, the lid 28 may be configured to be hingedly connected to the body of the medication chamber 34 to allow access therein. The lid 28 may have a pin that extends into a slot on the medication chamber 34 for closing and connection therewith. The drug guide 32 is also removable from the medication chamber 34. Such devices may be removed for cleaning, for example. Also, chamber lid 28 may be removed such that a patient or user may add liquid medication into the medication chamber 34.

Medication chamber 34 holds a liquid 52 containing a medication, drug, or other therapeutic substance therein. The liquid 52 may be transferred to medication chamber 34 via a pipette, or medication chamber 34 may comprise a disposable medication assembly (pre-sealed) which includes medication or substance in the form of liquid 52 therein. Medication chamber 34 and guide 32 are used to direct the liquid medication or substance 52 towards horn device 20. Medication chamber 34 is placed over the horn device 20 and secured in the lower portion 12 adjacent sensor port cover 23, for example. As shown in FIG. 2, the horn device 20 extends from an extension 21 of the lower portion 12 and is configured to fit into medication chamber 34 through an opening (not shown) at a bottom portion of the chamber body.

The horn device 20 is in communication with a vibrator 44 that is communication with circuitry (e.g., connected to a printed circuit board) and a controller (not shown) contained within the body of the lower portion 12. Vibrational force of the vibrator 44 is transmitted to the horn device 20 which is in contact with the medication chamber 34. Accordingly, the horn device 20 and vibrator 44 are configured to ultrasonically vibrate a flexible membrane 38 in the medication chamber 34 to form an aerosol of the medicine or substance to be ejected therefrom. Such vibration pushes a liquid medication 52 through the flexible membrane 38 to form an aerosol 62.

As shown in detail in FIG. 5, spring element 48 has its outer periphery positioned against vibrator 44. The vibrator 44 delivers ultrasonic vibrations (or oscillations) to the spring element 48 and thus the flexible membrane 38 when the devices are in contact with each other. The vibrator 44 may be a piezoelectric element in the form of a ring or disc and formed of any number of materials. In an embodiment, the piezoelectric element may be formed from a lead-based material such as lead zirconium titanate (PZT). The spring element 48 may be circular, disc-shaped, or otherwise shaped, and attached or connected to the vibrator 44. For example, in an embodiment, the spring element 48 is adhered to the vibrator via glue (e.g., epoxy). An opening is provided in the spring element 48 that is covered by flexible membrane 38 when assembled for use. The spring may be made of soft magnetic (non-magnetized, but attracted to magnets), hard magnetic (magnetized) or non magnetic material. In an embodiment, the spring element 48 is made of a stainless steel material or other metal. For purposes of this disclosure, the term "magnetic" is defined as a material that is attracted by magnets. The term "magnetized" is defined as an element that is a magnet and that has a remnant magnetic field (which attracts magnetic materials). In some cases, a magnetic material may be defined by a specific polarity and/or field configuration with respect to other magnetic or magnetized materials. Thus, the generic term magnetic refers to both magnetized materials as well as materials that are attracted to magnets. A soft magnetic material and magnet will be attracted to one another. Additionally and/or alternatively, electromagnetic materials may be used and provided as either a soft magnetic element (when no current is flowing) or a magnet (when current is flowing). The use and combination of materials for the herein described element should not be limited. Further description regarding embodiments using magnetic and magnetized materials is provided below.

The flexible membrane 38 may be a mesh or sieve that is provided in medication chamber 34. Flexible membrane 38 comprises a first (upper) surface 40 and a second (lower) surface 42 and has a plurality of apertures extending therethrough. The apertures of the flexible membrane 38 may be of any shape (e.g., conical, tapered) and/or any size and such embodiments are within the scope of this disclosure. In an embodiment, the apertures are conical in shape, with a circular cross-section comprising a diameter of 25 micrometers (μm) at the second surface 42 (e.g., liquid 52 input side) and circular cross-section comprising a diameter of 3 micrometers (μm) at the first surface 40 (e.g., aerosol output side). The apertures assist in creating an aerosolized form 62 of the liquid medication 52. The flexible membrane 38 may comprise any number of materials. In one embodiment, the flexible membrane 38 is made from a non-magnetic material. For example, the membrane 38 may be made from a polyimide material such as Kapton. In another embodiment, the membrane can a (soft) magnetic material such as Nickel or a Nickel-Palladium alloy.

The first (upper) surface 40 of flexible membrane 38, when assembled, is in fluid communication with mouthpiece 36. The second (lower) surface 42, when assembled, is in fluid communication with the liquid 52 contained in chamber 34. Referring back to FIG. 5, for example, the flexible membrane 38 can be positioned adjacent the spring element 48 so that it may receive vibration from the spring element 48 which is vibrated by the vibrator 44 (e.g., piezoelectric ring). This way, when liquid medication 52 is adjacent the second (lower) surface 42 of the flexible membrane 38 and the membrane 38 is vibrated, the liquid medication 52 will be transferred through the apertures towards the first (upper) surface 40 and ejected as an aerosol 62 to mouthpiece 36 for inhalation. The vibration or oscillation of the vibrator 44 is in a generally horizontal direction (as indicated in FIG. 3 by arrow A), while the spring element 48 and flexible member 38 move (vibrate) in a generally vertical direction (as indicated in FIG. 3 by arrow B).

As discussed above, the flexible membrane 38 may become contaminated or deteriorated over time with use. The disclosed configuration provides a removable and disposable membrane 38 without having to pollute the environment (e.g., with the lead material (e.g., lead zirconium titanate (PZT)) or other materials) of the vibration (piezoelectric) element 44.

In apparatus 10 a magnetic coupling member 54 may be provided that is configured to removably attach the flexible membrane 38 and the oscillating spring element 48 together. Magnetic member 54 may of any shape that permits it to be attached to membrane 38 while allowing membrane 38 to vibrate to generate aerosol. In an embodiment, the magnetic coupling member 54 and membrane 38 are formed as a single, inseparable element. In another embodiment, the magnetic coupling member 54 and membrane 38 may be removably attached to each other.

In one embodiment, magnetic member 54 is in the shape of a ring. Magnetic member or ring 54 is provided on one of the first surface 40 or the second surface 42 of the flexible membrane 38. In the illustrated embodiment, the magnetic ring 54 is provided on the first (upper) surface of the flexible membrane 38. In embodiments, the flexible membrane 38 may include a (soft) magnetic ring 54 glued to it, deposited on it, or grown on it by galvanic means. In one embodiment, the magnetic force between magnetic ring 54 and membrane 38 (which can be made from a material that is attracted to magnetic ring 54) alone secures the magnetic ring 54 to membrane 38. The magnetic ring 54 is configured to magnetically couple the flexible membrane 38 to the vibrator 44 (e.g., by way of spring element 48, as shown in FIG. 5A, which can be formed of a material that is magnetically attracted to magnetic ring 54) for delivery or ejection of a flow of aerosol droplets of the liquid 52 through the plurality of apertures. The magnetic ring 54 provides a magnetic force to hold membrane 38 to the spring element 48.

In another embodiment, magnetic ring 54 may be removably and magnetically coupled with another element in the apparatus. For example, a second magnetic member 64 may be provided in apparatus 10, as shown in FIGS. 5B and 5C, that magnetically couples with magnetic ring 54 to thereby couple the flexible membrane 38 to the vibrator 44. Second magnetic member 64 may comprise any number of magnetic or magnetized materials and should not be limiting. In an embodiment, second magnetic member 64 comprises a NdFeB material. Second magnetic member 64 can be formed in the shape of a ring (or other shape) and mounted with respect to nebulization chamber 46 so that magnetic ring 54 may be magnetically attracted to magnetic member 64. Second magnetic member 64 may be mounted below spring element 48 (e.g., adjacent the second (lower) surface). In an embodiment, second magnetic member 64 may be spaced a distance from spring element 48 such that it does not touch either the spring element 48 or membrane 38. while still attracting magnetic ring 54.

The magnetic force used to attract the membrane 38, spring element 48, magnetic ring 54 and/or second magnetic member 64 in the above embodiments may be determined based on the materials used to form each of the elements. For example, in the exemplary embodiment shown in FIG. 5A, the spring element 48 may be made of a material that is magnetic or magnetized. (Thus, the second magnetic member 64 as shown in FIG. 5B, for example, need not be provided, because the spring element 48 can directly attract the magnetic ring 54 thereto.)

Alternatively, in an embodiment wherein the spring element 48 is made of non-magnetic material, second magnetic member 64 could be provided so that the magnetic ring 54A can be magnetically coupled to the vibrator 44 in the apparatus 10, such as shown in FIG. 5B. If the membrane 38 is made of a soft magnetic material, the magnetic ring 54A may be formed of material(s) that are directly attracted to the material(s) of the second magnetic member 64. In an embodiment, if the magnetic ring 54A is made of a soft magnetic material, the second magnetic member 64 may comprise material(s) that may enable the magnetic ring 54A to be indirectly attracted to the second magnetic member 64.

In an embodiment, if the second magnetic member 64 is magnetized, (i.e., produces a magnetic field), then magnetic ring can be made of magnetic material(s). Alternatively, in an embodiment, magnetic ring 54 may be made of a magnetized material and second magnetic member 64 may be made of a magnetic material.

In yet another embodiment, as shown in FIG. 5D, the spring element 48 may comprise a magnetized material and membrane 38 can be made of magnetic material(s). Thus, the flexible membrane 38 may be directly attracted to the spring element 48. In another embodiment, the spring element 48 may comprise non-magnetic or soft magnetic material. Therefore, in an embodiment, second magnetic member 64 may be provided, as shown in FIG. 5E. If the flexible membrane 38 comprises a magnetic material, a second magnetic member 64 may comprise a magnetized material. Vice versa, if the membrane 38 is magnetized, then the second magnetic member 64 can be made of magnetic material(s).

In the above embodiments, magnetic ring 54 enables the flexible membrane 38 to be exchanged during cleaning, for example. However, it is also within the scope of this disclosure that magnetic ring 54 need not be provided with flexible membrane 38 in apparatus 10, as shown by the exemplary embodiments of FIGS. 5D and 5E. The upper portion 14 of the nebulizer 10 can be disassembled from the lower portion and its additional parts may be detached to clean the device and change the flexible membrane 38. Particularly, the chamber lid 28 and flexible membrane 38 may be separated from the other components of the nebulizer 10. The flexible membrane 38 may be removed and replaced, as needed, by breaking the magnetic force coupling the membrane 38 and vibrator 44 together.

In an embodiment, a removable insert 30 (shown in greater detail in FIGS. 3 and 4) may be provided in upper portion 14 that is configured to be removably inserted therein. In one embodiment, removable insert 30 has the flexible membrane 38 attached thereto. The removable insert 30 is positioned with respect to the nebulization chamber 46 and mouthpiece 36 such that the flexible membrane 38 is in contact with and engages the spring element 48 (e.g., due to existing magnetic forces) when assembled for use. As shown in FIGS. 3 and 4, the removable insert 30 may comprise a body 31 that is formed and shaped to fit or slide within walls of the upper portion 14. A bottom part 33 of the body 31 may have the magnetic ring 54 attached thereto.

In an embodiment, the magnetic ring 54 may be attached to the bottom part 33 of the removable insert body 30 via an attachment member 56, which may be in the form of a spring, a set of springs, tubes, or bellows. For example, the attachment member 56 may be of circular or disc shape and attached to the bottom part of the body, such as shown by the spring 56 in FIG. 4. In an embodiment, the attachment member 56 may comprise a set of two or more separate wires (or elastic bands or springs) secured around a circumference of and attached to magnetic ring 54 at one end and removable insert 30 on the other. The attachment member 56 may be provided as an integral part of the body of insert 30 or adhered (e.g., via glue) to a part of the insert 30. For example, in an embodiment wherein attachment member 56 is an integral part of the insert 30, the insert 30 may comprise a number (e.g., 3 or 4) of radial strips that are folded to form a concertina spring 56A as shown in FIG. 5C. The strips of concertina spring 56A may be glued at one end to bottom part 33 of insert 30 and secured at other end to magnetic ring 54.

The attachment member 56 may be provided such that the flexible membrane 38 and magnetic ring 54 are capable of vibrating as well as allowing an aerosolized drug therethrough. Therefore, the removable insert 30 with the magnetic ring 54 attached thereto allows for the flexible membrane 38 to be removed from the medication chamber assembly 26 and exchanged. Its construction also centers the flexible membrane 38 with respect to the opening of the spring element 48 such that the membrane 38 may be pulled into position by magnetic forces present close to the spring element 48 (e.g., via the spring element 48 itself or second magnetic member 64). In an embodiment, the suspension of the attachment member 56 is light-weight.

For example, in an embodiment, the entire insert 30 may be removed and replaced with a new insert 30 with a new, unused or clean flexible membrane 38 and magnetic ring 54 attached thereto. In another embodiment, the flexible membrane 38 may be removed from the insert 30 and replaced with a new, unused or clean flexible membrane 38. In another embodiment, both of the flexible membrane 38 and magnetic coupling ring 54 may be removed and replaced.

In an embodiment, the magnetic coupling ring 54 may have a thickness between approximately 0.2 and approximately 50 microns, depending on the magnetic susceptibility of the magnetic material and the size of the ring, none of which should be limiting. In one embodiment, the magnetic coupling ring 54 may have a thickness of approximately 1 micron. In an embodiment, a magnetic ring 54 made of iron can have a relative permeability on the order of 5000. Alternatively, a magnetic ring 54 made of nickel may have a relative permeability on the order of 600, or made of ferrite T38 on the order of 10000, and or made of Kovar (Fe54Ni29Co17) on the order of 1000-5000. In an embodiment, magnetic ring 54 may be made of Neoflux (NiFeB) material or an Fe/Ni material.

When assembled, the lower portion 12 and upper portion 14 encapsulate the medication chamber assembly 26. Also provided therein is removable insert 30 with the flexible membrane 38 attached thereto. FIG. 6 illustrates an example of the assembly of vibrator 44 with spring 48, magnetic ring 54, and flexible membrane 38 as described with respect to FIG. 5. Each part may be generally circular or generally annular in shape and formed to stack atop each other, as shown in the assembly of FIG. 7.

In an embodiment, the spring element 48 is made from a material such that a magnetic force attracts the magnetic coupling ring 54 to the spring element 48. The second (lower) surface 42 of the flexible membrane 38 may contact a top surface of the spring element 38 (as well as a top surface 20a of the horn 20). The spring element 48 may be also positioned against an o-ring 50 in lower portion 12, as shown in FIGS. 3 and 4, for example. Additional o-rings 58A and 58B or other seals may be also be provided to secure the upper and lower portions 14 and 12 together, respectively, as well as to generally secure the parts (e.g., spring element 38 and vibrator 44) therein. For example, o-rings 50 and 58A assist in suspending the spring element 48 by clamping the spring element 48 therebetween. O-ring 50 also aids in keeping liquid 52 away from spring element 48 and any associated electronic parts (e.g., electrodes) so that damage is not incurred.

The vibrator 44 is structured to vibrate (or oscillate) when driven by circuitry contained within the body of lower portion 12. For illustration purposes only, FIG. 3 generally indicates that a driving voltage may be provided to the vibrator 44 via circuitry 60. In the embodiment using a piezoelectric material, the applied voltage by circuitry 60 causes the piezoelectric material 44 to expand and contract in a generally horizontal motion (as indicated by arrow A). In response to this motion, the spring element 38 will leverage the vibration or oscillation to the flexible membrane 38 in a generally vertical manner (as indicated by arrow B). A vibratory motion caused by the oscillation of the piezoelectric element 44 is also transferred to the horn 20. The vibratory motion causes the liquid 52 within chamber 34 and adjacent flexible membrane 38 to pass through the apertures. The liquid medication leaving the apertures at the first (upper) surface 40 of the mesh 28 is aerosolized. Upon ejection from the apertures, the aerosolized liquid 62 passes from the first surface 40 and into mouthpiece 36. The aerosolized liquid 62 can then be inhaled by a patient through mouthpiece 36.

The magnetic coupling member in any of the embodiments discussed herein allows for replacement of the flexible membrane 38, without wasting or disposal of the vibrator 44.

The herein described illustrated embodiment of a magnetic coupling ring 54 should not be limiting. For example, in an embodiment the magnetic coupling ring 54 is attached to the second (lower) surface 42 of the flexible membrane 38 for removable attachment to the spring element 48 and vibrator 44.

In another embodiment, the flexible membrane 38 may be attached to the removable insert 30 (e.g., via attachment member 56). In such an embodiment, the magnetic ring 54 would not be attached to the removable insert 30 as shown in FIGS. 3 and 4. Rather, the flexible membrane 38 may comprise an alternate member that allows for the membrane 38 to be removably attached to the spring element 48 without having the magnetic ring 54 attached thereto. For example, the flexible membrane 38 may have a magnetic material coated thereon (e.g., at least in a location that would allow a connection to the magnetic coupling ring 54). Thus, the magnetic material coating of the flexible membrane 38 could be attracted to the spring element 48 when the removable insert 30 is placed in the apparatus 10.

In any case, the order and connection of any of the elements described herein should be such that the flexible membrane 38 will be magnetically attracted by the spring element 48 of the apparatus 10.

The apparatus 10 described herein may be used for the treatment of cystic fibrosis, asthma and COPD (pulmonary arterial hypertension (PAH)), for example. Although discussed in the context of the nebulizer 10 shown in the Figures, it is contemplated that the present invention may be utilized with other nebulizers and/or devices. Also, apparatus 10 is designed to work with any aerosol of any common particle size and the particle size distribution should not be limited. In an embodiment, the mean aerosol particle size is 0.1 to 10 micrometers. In another embodiment, the mean aerosol particle size is 0.5 to 5 micrometers. In yet another embodiment, the aerosol particle size is submicron size. An example of particles with submicron size is nanoparticles.

In an embodiment, removable insert 30 may comprise a smaller configuration, or not provided at all. For example, in an embodiment the insert 30 may comprise body 31 that is formed and/or shaped to fit with respect to the lower portion 12, so as long as the flexible membrane 38 and spring element 48 are connected to each other. Also, the body 31 does not need to be formed such that it fits or slides within or directly adjacent walls of the upper portion 14 and/or lower portion 12. Alternatively, in another embodiment, the flexible membrane 38 and magnetic coupling ring 54 may not include a removable insert 30, and may be removable from the apparatus 10 by grasping the membrane 38 and/or ring 54 directly to break the magnetic connection.

Also, it should be noted that the above described features of apparatus 10 are not meant to be limiting. Furthermore, other known features, which may not have been described in detail herein, should not be limiting. For example, the number of treatments and/or treatment time(s) should not be limited. Also pressure, flow rate, operating pressure, operating flow rate, and frequency of dosage of the medication/liquid for apparatus 10 is not limited.

Flexible membrane 38 may have any number of apertures or micropores of any size. In an embodiment, for example, the membrane may comprise a mesh that comprises 5000-6000 holes that are 3 microns in size. Moreover, the use of flexible membrane 38, magnetic member 54, and/or other elements as described above is not meant to be limited to use with an apparatus 10 that is used for medical treatment. For example, it is envisioned that such features may be used in an appliance that is configured to deliver an aerosol as other forms of treatment. The flexible membrane 38 and magnetic member 54 may be used in household appliances. In an embodiment, the features may be used in an apparatus for moisturizing textiles, such as in steam ironing with an iron. Alternatively, such features may be used in alternate devices for steam delivery (e.g., humidifying devices), devices for cleaning, and the like.

A patient is a person to whom it is desired that an inhaled pharmaceutical aerosols be delivered; the definition of the term "patient" includes both a sick person as well as a healthy person.

The threshold of mist formation may be at a driving voltage of 10 Volts peak-to-peak, at 98 kHz. In some cases, materials or elements that may come into contact with the liquid 52 may have to be covered or coating with a shielding layer to prevent deterioration. For example, materials such as Nickel, Gold, or any other suitable, non-toxic and non-corrosive material may be applied in the form of a layer on one or more elements.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. An apparatus for aerosol delivery of a substance, the apparatus comprising:
   a mouthpiece;
   a chamber for holding a liquid substance therein;
   a flexible membrane comprising a plurality of apertures therethrough; and
   a vibrator for vibrating the flexible membrane, wherein the vibrator includes a piezoelectric element;
   wherein the flexible membrane comprises a magnetic material that enables the flexible membrane to be magnetically coupled to the vibrator such that when the flexible membrane is vibrated by the vibrator a flow of aerosol droplets of the substance are ejected through the plurality of apertures and to the mouthpiece for delivery therefrom.

2. An apparatus according to claim 1, wherein the flexible membrane comprises a magnetized material.

3. An apparatus according to claim 1, further comprising a spring attached to the vibrator configured to couple the flexible membrane to the vibrator, and wherein the spring comprises a magnetized material.

4. An apparatus according to claim 1, further comprising a magnetic member positioned adjacent to the vibrator, the magnetic member being configured to magnetically couple the flexible membrane to the vibrator.

5. An apparatus according to claim 4, wherein the magnetic member comprises a magnetized material.

6. A removable insert configured to be removably inserted into an apparatus for aerosol delivery of a substance, the apparatus comprising a vibrator, wherein the vibrator includes a piezoelectric element, the removable insert comprising:
- a body, and
- a flexible membrane attached to the body, the flexible membrane comprising a plurality of apertures therethrough;
- the flexible membrane further comprising a magnetic material that enables the flexible membrane to be magnetically coupled to the vibrator when the removable insert is inserted into the apparatus,
- wherein, when the flexible membrane is vibrated by the piezoelectric element included in the vibrator, a flow of aerosol droplets of the substance are ejected through the plurality of apertures for delivery out of the apparatus.

7. The removable insert according to claim 6, further comprising an attachment member for attaching the flexible membrane to the body.

8. The removable insert according to claim 7, wherein the attachment member comprises at least one spring.

9. The removable insert according to claim 6, further comprising a magnetic member configured to magnetically couple the flexible membrane to the vibrator.

10. The removable insert according to claim 9, wherein the magnetic member is attached to the flexible membrane.

11. An apparatus for aerosol generation, the apparatus comprising:
- a chamber for holding a liquid substance therein;
- a flexible membrane comprising a plurality of apertures therethrough;
- a vibrator for vibrating the flexible membrane, wherein the vibrator includes a piezoelectric element; and
- a magnetic member configured to magnetically couple the flexible membrane to the vibrator such that when the flexible membrane is vibrated by the piezoelectric element included in the vibrator a flow of aerosol droplets of the liquid substance are ejected through the plurality of apertures.

12. The apparatus according to claim 11, wherein the piezoelectric element is in the form of a ring.

13. The apparatus according to claim 11, wherein the flexible membrane comprises a non-magnetic material.

14. The apparatus according to claim 11, wherein the flexible membrane comprises a magnetic material.

15. The apparatus according to claim 11, wherein the magnetic member is attached to the flexible membrane.

16. The apparatus according to claim 15, wherein the magnetic member is attached to the flexible membrane via an adhesive.

17. The apparatus according to claim 11, wherein the magnetic member is deposited on the flexible membrane.

18. The apparatus according to claim 11, wherein the magnetic member is a spring.

19. The apparatus according to claim 18, wherein the spring is attached to the vibrator.

20. The apparatus according to claim 11, wherein the magnetic member is magnetically coupled to a spring attached to the vibrator.

21. The apparatus according to claim 8, wherein the at least one spring is formed of magnetic material.

22. The apparatus according to claim 21, wherein the at least one spring includes stainless steel.

23. The apparatus according to claim 11, wherein the flexible membrane is attached to a removable insert that is configured to be removably inserted into the apparatus.

24. The apparatus according to claim 11, wherein flexible membrane comprises a polyimide material.

25. The apparatus according to claim 11, further comprising a second magnetic member positioned adjacent to the vibrator, the second magnetic member configured to magnetically couple with the magnetic member.

26. The apparatus according to claim 11, wherein the magnetic member comprises a magnetized material.

27. The apparatus according to claim 11, wherein the magnetic member comprises a non-magnetized material.

28. The apparatus according to claim 26, further comprising a second magnetic member positioned adjacent to the vibrator, the second magnetic member configured to magnetically couple with the magnetic member.

29. The apparatus according to claim 28, wherein the second magnetic member comprises a magnetized material.

30. The apparatus according to claim 27, further comprising a second magnetic member positioned adjacent to the vibrator, the second magnetic member configured to magnetically couple with the magnetic member.

31. The apparatus according to claim 30, wherein the second magnetic member comprises a magnetized material.

* * * * *